United States Patent [19]

Zaiger

[11] Patent Number: Plant 6,071

[45] Date of Patent: Dec. 29, 1987

[54] PLUM TREE (34EA305N)

[76] Inventor: Chris F. Zaiger, 537 Rosemore Ave., Modesto, Calif. 95351

[21] Appl. No.: 814,730

[22] Filed: Dec. 30, 1985

[51] Int. Cl.[4] ..... A01H 5/03

[52] U.S. Cl. ..... Plt./38

[58] Field of Search ..... Plt./38

*Primary Examiner*—Robert E. Bagwill

[57] ABSTRACT

A new and distinct variety of plum tree which has the following unique combination of outstanding features:

1. Large size fruit.
2. Vigorous and upright growth.
3. Relatively uniform ripening of the fruit throughout the tree.
4. The fruit having excellent eating quality.
5. The regular and heavy production of fruit.

1 Drawing Figure

ORIGIN OF THE VARIETY

The new variety of plum tree was originated by me in my experimental orchard located at Modesto, Calif. as an open pollinated seedling of seed collected from Red Beaut Plum (U.S. Plant Pat. No. 2,539). A large number of open pollinated seedlings were grown under careful observation and gave varying characteristics, one such seedling, having especially desirable fruit characteristics was selected for reproduction and commercialization.

ASEXUAL REPRODUCTION OF THE VARIETY

The present variety of plum tree was asexually reproduced by budding in my experimental orchard located at Modesto, Calif. and shows that said characteristics run true to the original tree and are established and transmitted through succeeding propagations.

SUMMARY OF THE VARIETY

A new and distinct variety of plum tree, which is of large size, vigorous, upright growth and a regular and productive bearer of large, firm, clingstone fruit, characterized as to its novelty by its uniform size and maturity throughout the tree. The fruit of the new variety is further characterized by maturing in early July, approximately one month after Red Beaut Plum (U.S Plant Pat. No. 2,539) and having an attractive yellow skin color, excellent flavor and good shipping quality.

BRIEF DESCRIPTION OF THE PHOTOGRAPHS

The accompanying photographs show typical specimens of the foliage and fruit of the present variety, such illustrations being of a twig with the upper and lower surface of the leaves being shown, and typical specimens of the fruit showing exterior skin color with one fruit being divided in the suture plane to show the flesh color and the stone remaining in place.

DESCRIPTION OF THE VARIETY

The following is a detailed botanical description of the new variety of plum tree and its flowers, foliage and fruit based on observations of specimens grown at Modesto, Calif., with color terminology (except those in common color terms) in accordance with Reinhold Color Atlas by A. Kornerup and J. H. Wanscher.

Tree:

*Size.*—Large.
*Vigor.*—Vigorous.
*Growth.*13 Upright.
*Density.*—Medium dense.
*Shape.*—Pruned to vase shape.
*Production.*—Productive.
*Bearer.*—Regular bearer.

Trunk:
*Size.*—Medium.
*Texture.*—Shaggy.

Branches:
*Size.*—Medium.
*Texture.*—Medium rough.
*Color.*—Grayish brown to reddish brown.

Leaves:
*Size.*—Large. Average length — 5½". Average width — 2½".
*Shape.*—Oblanceolate. Tip-acuminate.
*Margin.*—Serrate.
*Texture.*—Smooth on upper surface. Raised ribs and mid-ribs on lower surface.
*Color.*—Upper surface — grayish green to dark green (28-E-8) to (28-F-8). Lower surface — dull green to grayish green (29-E-6) to (29-E-8).

Flower buds:
*Size.*—Small to medium.
*Length.*—Medium.
*Form.*—Plump. Free.

Flowers:
*Blooming period.*—Date of first bloom: Mar. 3, 1984. Date of full bloom: Mar. 8, 1984. Blooms approximately 7 days after Santa Rosa Plum. Varies slightly with climatic conditions.
*Size.*—Small to medium.
*Color.*—White.

Fruit:
*Maturity when described.*—Shipping ripe.
*Date of first picking.*—July 6, 1984.
*Date of last picking.*—July 11, 1984.
*Size.*—Large. Average diameter axially — 2½" to 2¾". Average transversely in suture plane 2⅛" to 2 5/16".
*Form.*—Heart shape. Flattened at stem end. Elongated at apex.
*Suture.*—Nearly smooth. Extends from base to apex.
*Base.*—Retuse.
*Apex.*—Elongated to give heart shape.

*Cavity.*—Rounded — slightly elongated in suture plane. Average depth — ⅜". Average breadth — 9/16".

*Stem.*—Medium length. Medium width.

Skin:

*Thickness.*—Medium.

*Texture.*—Medium.

*Tendency to crack.*—None.

*Down.*—Wanting.

*Bloom.*—Moderate.

*Color.*—Yellow to grayish yellow (3-A-7) to (3-B-8).

Flesh:

*Ripens.*—Fairly uniform, very slightly earlier at apex.

*Texture.*—Firm, fine melting.

*Flavor.*—Mild.

*Eating quality.*—Excellent.

*Color.*—Yellow (3-A-6) to (3-A-8).

Stone:

*Type.*—Clingstone.

*Size.*—Average length — 1". Average width — 11/16". Average thickness — ½".

*Color.*—Light brown (5-D-5) to (5-D-7).

*Base.*—Straight.

*Apex.*—Acuminate.

*Sides.*—Nearly equal.

*Surface.*—Slightly furrowed.

*Tendency to split.*—None.

Use: Local and long distance markets. Dessert.

Keeping quality: Good.

Shipping quality: Good.

The plum tree and its fruit herein described may vary in slight detail due to climatic, soil and ecological conditions under which it may be grown; the description is that of the variety grown under conditions at Modesto, Calif.

The following is claimed:

1. A new and distinct variety of plum tree of large size, vigorous upright growth and a regular and productive bearer of large, heart shaped, clingstone fruit; and further characterized by blooming approximately 7 days after Santa Rosa Plum (non-patented) and bearing fruit ripening approximately 30 days after Red Beaut Plum (U.S. Plant Pat. No. 2,539) and the fruit having an attractive yellow skin color, firm yellow flesh, excellent eating quality, and the ability to ship to long distance markets.

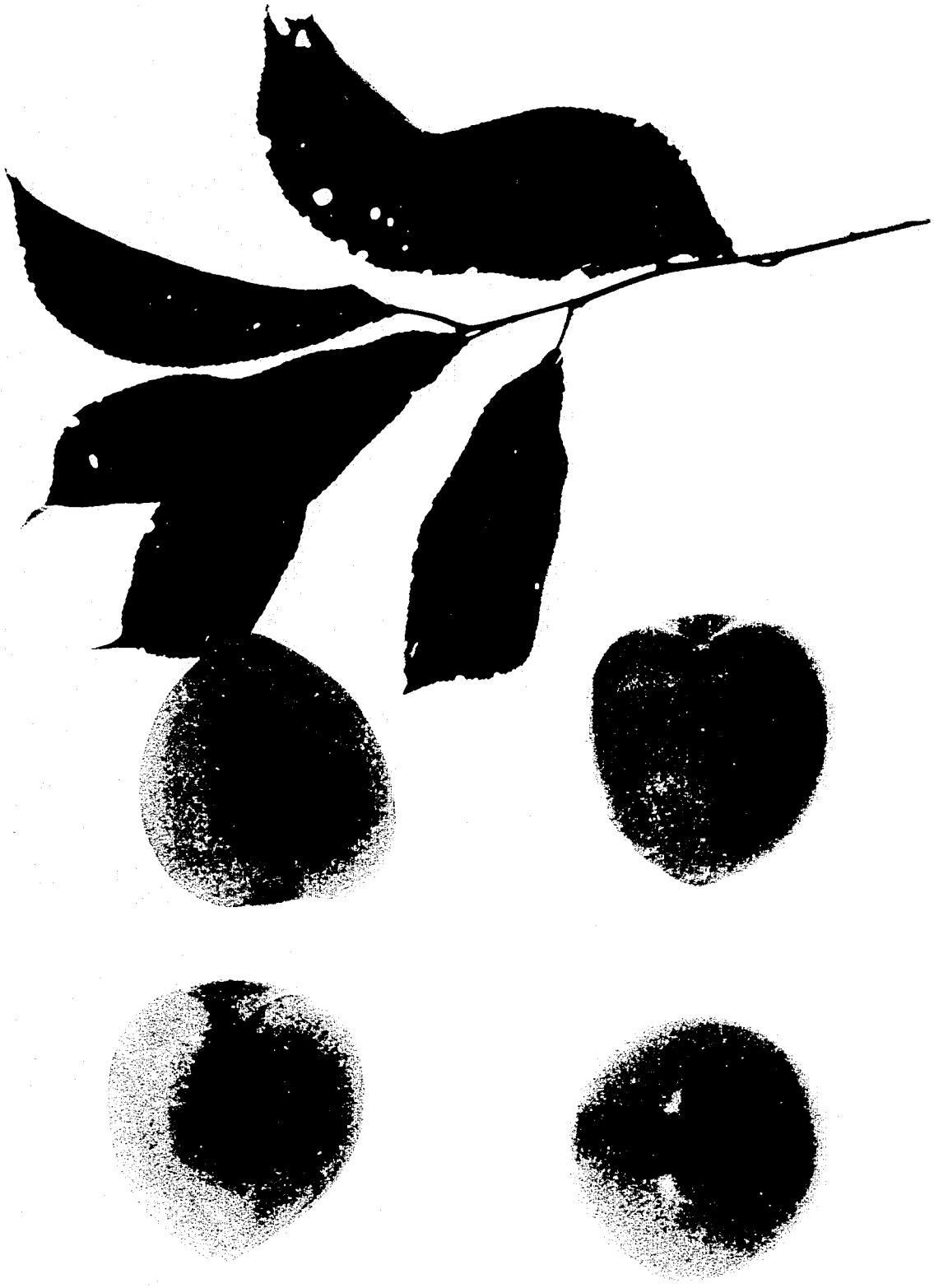

* * * * *